United States Patent [19]
Koch et al.

[11] Patent Number: 5,628,319
[45] Date of Patent: May 13, 1997

[54] METHOD AND DEVICE FOR THE NON-DESTRUCTIVE TESTING OF OBJECTS USING ULTRASONICS

[75] Inventors: Roman Koch, Hösbach; Thomas Kreutter, Goldbach, both of Germany

[73] Assignee: Nukem GmbH, Alzenau, Germany

[21] Appl. No.: 545,839

[22] PCT Filed: May 6, 1994

[86] PCT No.: PCT/EP94/01437

§ 371 Date: Nov. 13, 1995

§ 102(e) Date: Nov. 13, 1995

[87] PCT Pub. No.: WO94/27165

PCT Pub. Date: Nov. 24, 1994

[30] Foreign Application Priority Data

May 13, 1993 [DE] Germany .................. 43 15 794.7

[51] Int. Cl.[6] .................................................. A61B 8/00
[52] U.S. Cl. .................................................. 128/660.01
[58] Field of Search ............ 128/660.01, 660.07, 128/661.03, 661.01

[56] References Cited

U.S. PATENT DOCUMENTS

| | | | |
|---|---|---|---|
| 4,460,890 | 7/1984 | Busby | 364/726 |
| 4,913,157 | 4/1990 | Pratt, Jr. et al. | 128/661.03 |

FOREIGN PATENT DOCUMENTS

| | | |
|---|---|---|
| 471223 | 2/1992 | European Pat. Off. |
| 2505141 | 8/1975 | Germany . |
| 3242284 | 5/1984 | Germany . |
| 3632813 | 4/1987 | Germany . |
| 3640882 | 6/1988 | Germany . |
| 3822195 | 1/1990 | Germany . |
| 4040190 | 6/1992 | Germany . |

OTHER PUBLICATIONS

A. Klauer and M. Pandit, "Messignalverarbeitung mit hochaflösender AD–Wandlung", Technisches Messen tm, 52. Jahrgang, Heft Nov. 1985.

A. Duschek, "Vorlesungen über höhere Mathematik", Unveränderter Nachdruck der dritten, verbesserten Auflage, Springer–Verlag, 1965.

ROS et al: "Digital techniques improve range measurements with ultasound snesor", Sensors and actuators A, vol. A32, No. 1/3, Apr. 1992, pp. 550–554 XP287373.

Primary Examiner—Francis Jaworski

[57] ABSTRACT

The invention concerns a method and device for nondestructive testing. Ultrasonic pulses are fed into the object under test. Ultrasonic waves emerging from the object are detected by an ultrasonic test head, converted into electrical signal and amplified. The signals are then sampled to produce measurement values, which are digitized and stored. From the digitized sampled values of the signals a function is obtained by interpolation, by means of which the peak values of the ultrasonic waves and/or the time of propagation of the wave at the peak is determined.

7 Claims, 6 Drawing Sheets

METHOD AND DEVICE FOR THE NON-DESTRUCTIVE TESTING OF OBJECTS USING ULTRASONICS

BACKGROUND OF THE INVENTION

1. Field of the Invention

The invention relates to a method and a device for non-destructive testing of objects using ultrasonics, whereby ultrasonic pulses are introduced by an ultrasonic testing head into the respective object, and whereby ultrasonic waves are emitted by the object in response to the ultrasonic pulses introduced and are then picked up by an ultrasonic testing head and converted into electrical signals of a signal sequence.

2. Prior Art

In medical technology, an ultrasonic examination method for diagnostic purposes is known in which ultrasonic vibrations are introduced into a body to be examined that then generates ultrasonic echoes which are converted by an ultrasonic converter into electrical signals. The radiation direction of the ultrasonic vibrations is gradually changed in identical angular steps using mechanical or electronic means. An examination area in the body is limited by the two outer radiation directions. The ultrasonic echoes reflected along the paths preset by the radiation directions are converted into a sequence of measurement values that represent the reflection properties of the examination area at various measurement points that are associated with picture points of an ultrasonic image displayed on a monitor. For each picture point of the ultrasonic image, a picture value is calculated by interpolation of the measured values of those measurement points adjacent to the picture point as a result of the geometrical association between the examined area and the ultrasonic image (DE 36 40 882 A1).

In medical technology, a method is also known for delay determination of ultrasonic pulses passing through an examined area and converted by an ultrasonic converter into an electrical measurement signal. After emission of the ultrasonic pulse, the time that passes until the measurement signal has reached a preset threshold is measured. The measurement signal is amplified and fed to an analog/digital converter working with a predetermined sampling rate. The sample values of the analog/digital converter are stored. An excerpt from the measurement signal formed by a sequence of sample values is compared with an identical-length excerpt of a reference signal stored as a sequence of reference values. The excerpt of the reference signal and if necessary that of the measurement signal are displaced one node at a time until the displaced sections match up best when they are again compared with one another. The delay is determined by a digital processor, which can also have controlling function, by correction of the period thus ascertained. The sequence of reference values, which is if possible precisely proportional to the sample values of the excerpt, is found with a function which is a yardstick for the divergence of the measurement signal excerpt scaled with one factor from a correspondingly long excerpt of the reference signal (DE 32 42 284 A1).

Also known is an ultrasonic imaging device for medical diagnostic technology, having an ultrasonic converter that introduces an ultrasonic beam into a body in order to achieve sector sampling. The ultrasonic converter converts ultrasonic echo waves into echo signals that are sampled in intervals that are shorter than the division of the pixels or picture elements. The measurement values sampled along each sampling line are stored as pixel data. The data disposed at those points of two adjacent sampling lines that are identically spaced from a beam emission point are used to obtain interpolation data (DE 36 32 813 A1).

In a known method for determining the amplitude and the amplitude position of the maximum of a correlation signal, a correlator is supplied with a digitalized picture signal and a digitalized reference image. The correlator generates the correlation signal, which is passed to a memory with maximum detector that calculates the amplitude and the amplitude position. The calculated values are then interpolated in order to determine the real maximum of more closely approximated values (DE 38 12 195 A1).

Finally, it is known in measurement signal processing with high-resolution analog/digital converters to filter the analog signals with low limit frequency and to conduct the analog/digital conversion with high resolution (periodical: Technisches Messen tm, 52nd year, issue 11, 1985, pages 404–410).

It is furthermore known to interpolate discrete values of a function by polynomials (Book: A. Duschek: "Vorlesungen über höhere Mathematik", 4th edition 1965, pages 297–301, Vol. 1).

Important characteristic quantities for an ultrasonic instrument for non-destructive materials testing in automated testing facilities are the speed and the accuracy with which crack fault signals and wall thickness signals received from fault echoes generated using the ultrasonic pulse echo method or from a rear-wall echo sequence can be picked up.

Accordingly, the quality of a ultrasonic instrument hinges on the amplitude and delay resolution achieved with a pulse sequence frequency as high as possible. By amplitude resolution we understand the accuracy with which the amplitude extreme is ascertained (positive maximum or negative minimum), or the positive or negative maximum pulse peak. The delay is the time passing between the entry of the ultrasonic pulses into the object and the reception of the ultrasonic waves leaving the object.

In an analog ultrasonic instrument, various time intervals (windows) can be selected for evaluation of the signals received from a testing head or ultrasonic sensor after amplification. For each window, a peak value memory, using which the signal extreme within the window is recorded in analog form, is necessary for amplitude determination. In conventional systems, the signal thus obtained is then digitalized for further processing in a computer.

For measurement of the delay, an additional module is necessary. With the signal peak or the flank, in the case that the threshold within a window is exceeded, a digital counter is started which is stopped with the result within a second window. To achieve the required precision, high-frequency and hence expensive digital counters are necessary here. To improve the resolution, an additional analog time measurement is often integrated using a sawtooth signal. The sawtooth amplitude value achieved at the stop event is also digitalized and converted by a calibration unit into a delay.

In a digital ultrasonic instrument, the complete signal sequence received from an ultrasonic testing head or ultrasonic sensor is digitalized immediately after amplification. The amplitude and the delay are then determined from the digital data.

The accuracy with which high-frequency pulse-like signals can be determined by digital measurement value pickup is limited by the performance data of the analog/digital converter (ADC) used. The achievable accuracy when determining the amplitude of the maximum pulse peak is determined predominantly by the sampling rate (sampling frequency) of the ADC, beside the digitalization definition (bit number). The time position of the pulse maximum—precise knowledge of which is required for determining the delays—is determined solely by the available sampling rate.

The lower the ratio of sampling frequency to signal frequency, the poorer the resolution of the amplitude and delay determination. This means that to determine short wide-band and hence high-frequency pulses, very high sampling rates are necessary.

For achieving the required accuracy, technology normally applies methods (interleaved or random sampling) in which the same event must occur several times consecutively and then be digitalized at different times. To achieve the required accuracy in the case of events that occur once only, however, demands are placed on the ADC to be used (high digitalization and high sampling rate) and on the following-on memory modules (high speed and great depth) that are at present not feasible for price reasons on account of the very high expenditure involved.

If a commercially available analog-digital converter and standard memory modules are used, the sampling density of the signals is not sufficient for precise determination of the maximum signal amplitude and its timing.

SUMMARY OF THE INVENTION

This is where the invention comes in: the problem underlying the invention is to develop a method and a device for non-destructive testing of objects using ultrasonics, whereby with a preset sampling rate for the signals generated by an ultrasonic receiver the amplitude maximum and/or the delay of the amplitude maximum can be determined with high resolution.

The problem is solved for the method according to the invention in that measurement values are obtained from the signals of the signal sequence by time-equidistant sampling and then are digitalized and stored, and that a function represented by the discrete measurement values stored and digitalized is replaced by a Grade n polynomial according to the following equation:

$$P_N(t_i) = \sum_{n=0}^{N} a_n \cdot t_i^n, t_i = i\Delta t$$

where $t_i$ is the sampling time, for $i=0,1 \ldots N$, and $a_n$ the coefficients of the polynomial, and in that the amplitude extreme of the received ultrasonic waves and/or the delay of the ultrasonic waves with the amplitude extreme is determined using the polynomial. With the aid of the interpolation method, it is then possible to achieve a high resolution when determining the amplitude and the delay, even if commercially available modules are used for the digitalizer and the memories. In addition, the extent of the hardware is reduced compared with typical analog-operating ultrasonic testing systems. The amplitude and delay measurements can still be performed with the same hardware. The amplitude extreme is compared during further processing in particular with at least one preset threshold value that is characteristic for a fault.

By interpolation with the polynomial, the result can be obtained with relatively little calculation work.

It is expedient if the delay of the ultrasonic waves is determined with the amplitude extreme from the first derivation of the Grade N polynomial based on the time using the following equation:

$$\frac{\partial P_N}{\partial t} = \sum_{n=0}^{N} n a_n t^{(n-1)} = 0$$

and that the amplitude extreme is determined by incorporation of the delay value $t=t_0$ into the equation $$P_N(t_0) = \sum_{n=0}^{N} a_n \cdot t_0^n$$

of the polynomial.

The signals emitted by the ultrasonic testing head are preferably sampled with a sampling rate between 60 and 120 MHz and digitalized with a resolution of eight to twelve bits. These sampling rates can be achieved with commercially available sample and hold circuits. For resolutions up to 8 to 12 bits, commercially available analog/digital converters can be used.

In a favorable embodiment, the sample values are filtered to reduce fault effects.

A device for non-destructive testing of objects using ultrasonics, by which on the one hand ultrasonic pulses are introduced by an ultrasonic testing head into the respective object and on the other hand ultrasonic waves being emitted by the object are picked up by an ultrasonic testing head and converted into electrical signals of a signal sequence, where the device has an amplifier, an analog/digital converter, a write/read memory, a digital processor and a bus, consists in accordance with the invention in that a sample and hold circuit is connected in front of the analog/digital converter and operates with a sampling rate in the range from 60 to 160 MHz to generate from the electrical signals measurement values that are digitized by the analog/digital converter with a resolution of twelve bits and then stored in the write/read memory, and in that the discrete, stored and digitized measurement values form a function which is replaced by a Grade N polynomial according to the following equation:

$$P_N(t_i) = \sum_{n=0}^{N} a_n \cdot t_i^n, t_i = i\Delta t$$

where $t_i$ is the sampling times for $i=0.1 \ldots N$, and $a_n$ the coefficients of the polynomial, and in that the amplitude extreme of the ultrasonic waves and/or the delay of said ultrasonic waves with the amplitude extreme is determined using said polynomial. This array operates with a commercially available sample and hold circuit and a commercially available analog/digital converter. The higher resolutions of the amplitude and the delay can therefore be achieved in an economical manner.

Preferably, at least two devices each having an ultrasonic testing head for transmission and reception, an amplifier, one sample and hold circuit each, one write/read memory each and a processor are combined in one design unit. Since the hardware expenditure for evaluation of the signals generated by an ultrasonic receiver is relatively low, a number of such arrays can be provided parallel to one another for increasing the testing speed.

Since the complete signal curve is available in digital form, all the advantages of digital signal processing such as digital filtering or correlation can also be used for improvement of the accuracy.

Further details, advantages and features of the invention are clear not only from the claims and from the features they describe, singly and/or in combination, but also from the following description of a preferred embodiment.

DETAILED DESCRIPTION OF PREFERRED EMBODIMENTS OF THE INVENTION

Figure 1:
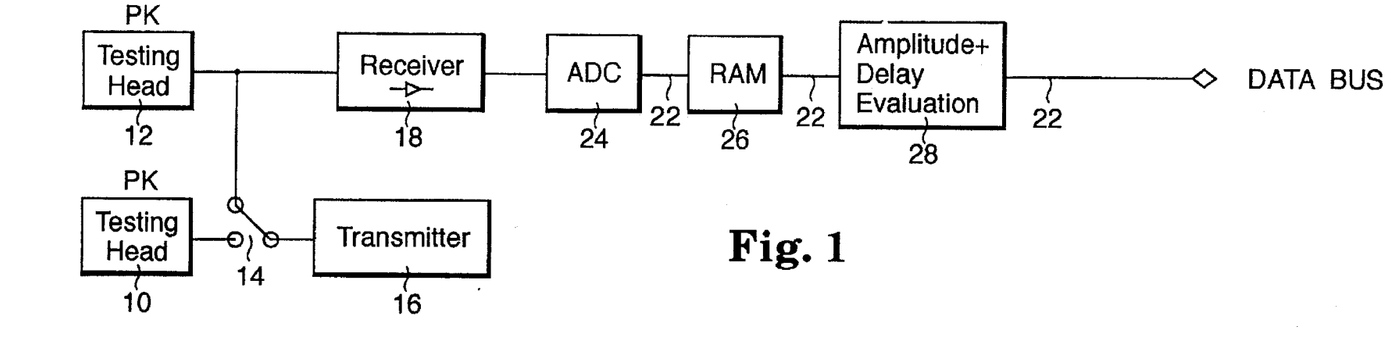
FIG. 1 shows a device for non-destructive testing of objects with digital processing of received ultrasonic signals in a block diagram.

A device for non-destructive testing of objects using ultrasonics is provided with an ultrasonic testing head (10) for transmitting pulse-like ultrasonic waves and an ultrasonic testing head (12) for receiving ultrasonic waves. The transmitter and the receiver for ultrasonic waves are frequently combined in one testing head. The electro-acoustic ultrasonic testing head (10) can be connected using a changeover switch (14) to a transmitter (16) that generates pulses or pulse groups. The transmitter (16) can also be connected to the ultrasonic testing head (12) using the changeover switch (14). An amplifier (18) is connected to the ultrasonic testing head (12), to which is connected a sample and hold circuit (20). The sample and hold circuits (20), an analog/digital converter (24), a write/read memory (26) and a processor (28) are connected using a data bus (22).

Figure 2:
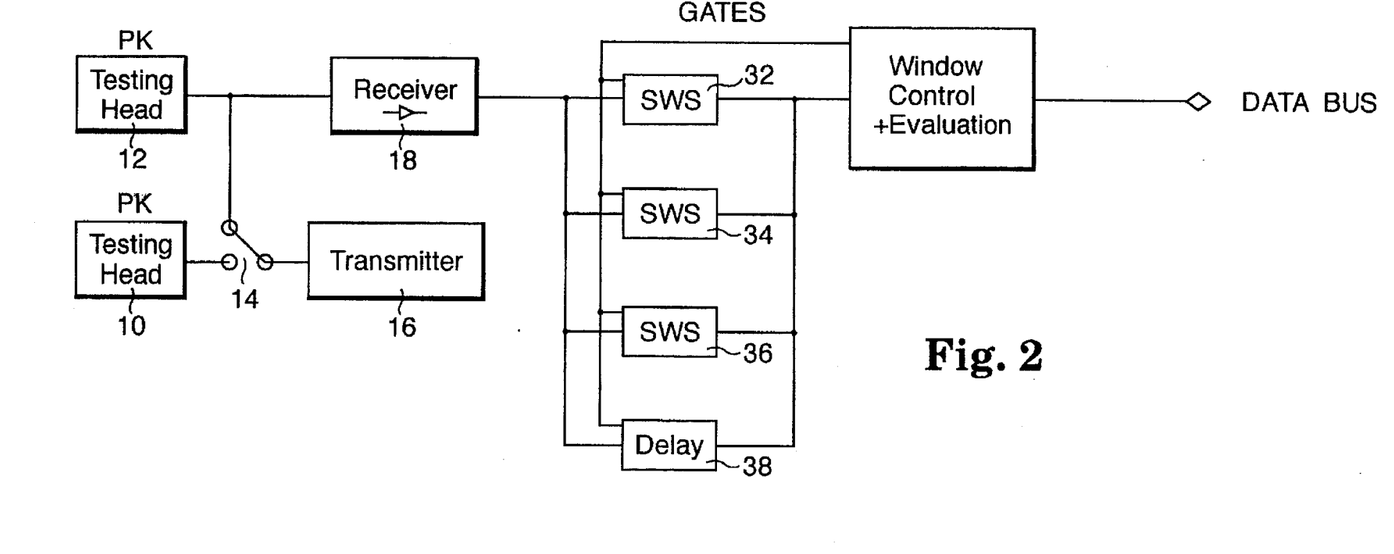
FIG. 2 shows a block diagram of a conventional, analog-operating device for non-destructive testing of objects.

FIG. 2 shows an analog-operating device for non-destructive testing of objects. The device according to FIG. 2 has, like the device shown in FIG. 1, the receiver (16), changeover switch (14), the two ultrasonic testing heads (10), (12) in the form of electro-acoustic converters, and the amplifier (18). Using a window control and evaluation unit (30), various time intervals (windows) the selectable for evaluation of the signals received from the ultrasonic testing head (12) after amplification. For each window, a peak value memory is necessary for amplitude determination. FIG. 2 shows three peak value memories (32), (34) and (36). With the respective peak value memory, the signal maximum within the window is picked up in analog form. The signal thus obtained can then be digitalized in a computer and further processed. For delay measurement, a module (38) is required in addition. When the threshold is exceeded within a window, a digital counter is started with the signal peak or flank, and stopped with the event within a second window. To achieve the required accuracy, high-frequency and hence expensive counters are necessary. To improve the resolution, an additional analog time measurement is often integrated using a sawtooth signal. The amplitude value of the sawtooth achieved at the stop event is also digitalized and converted into a delay by a calibration unit.

Figure 3:
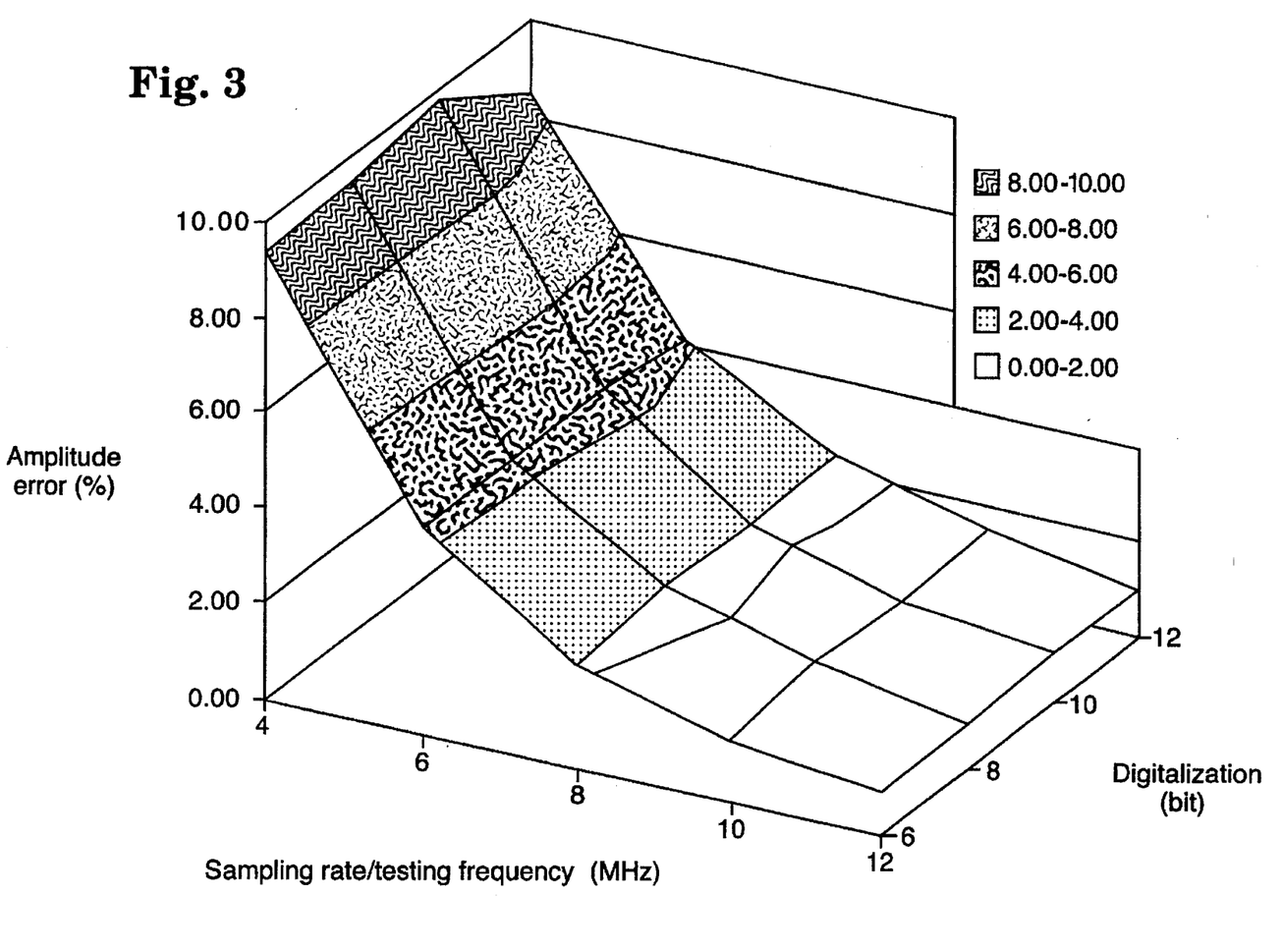
FIG. 3 shows a diagram of the theoretically possible amplitude resolution as a function of the sampling rate and the digitalization of an analog/digital converter.

With the ultrasonic testing instrument shown in FIG. 1, the signal sequence received from the ultrasonic testing head (12) is, after amplification, sampled, digitalized and stored. The amplitude maximum and the delay of the ultrasonic pulses until the amplitude maximum is received are determined from the stored data. FIG. 3 shows a three-dimensional diagram in which the amplitude error is shown in % as a function of the sampling rate in MHz and of the digitalization resolution in bits.

FIG. 3 shows that the achievable accuracy when determining the amplitude of the maximum pulse peak is determined predominantly by the sampling frequency of the sample and hold circuit or of the analog/digital converter, beside the digitalization resolution. The accuracy of the time position of the pulse maximum—precise knowledge of which is required for determining the delays—is determined solely by the sampling rate. The lower the ratio of sampling frequency to signal frequency, the poorer the resolution of the amplitudes and delays.

In the array shown in FIG. 1, commercially available components, e.g. a commercially available sample and hold circuit (20), a commercially available analog/digital converter (24) and a commercially available write/read memory (26) of RAM type are used. The analog/digital converter (24) has a resolution of 8–12 bits. The sampling rate (sampling frequency) of the sample and hold circuit and of the analog/digital converter is in the range from 60 to 160 MHz.

Figure 4:
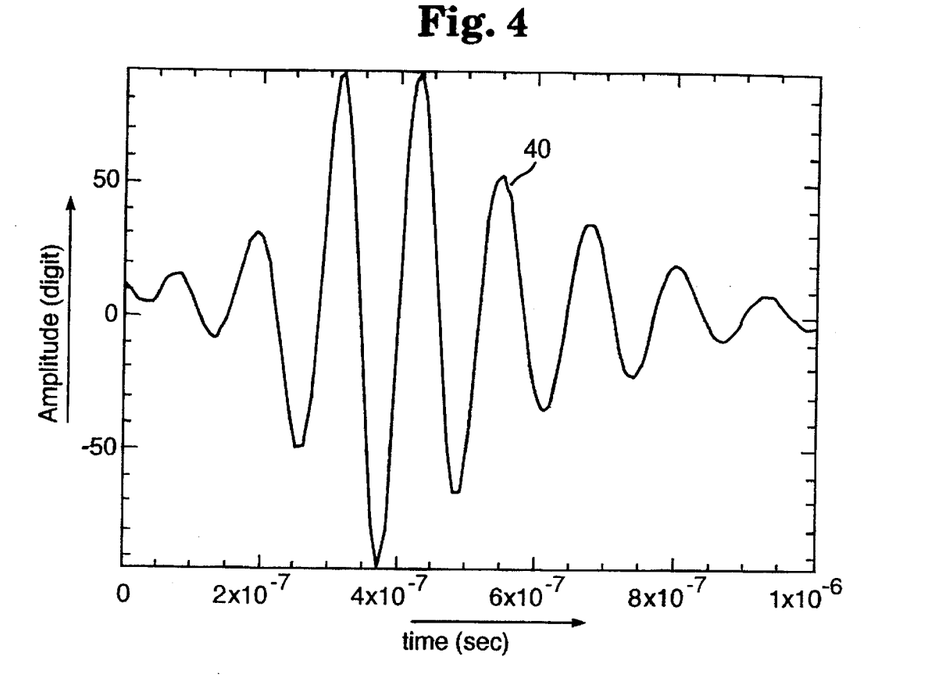
FIG. 4 shows a digitalized amplitude signal, received as a crack fault echo, of an ultrasonic receiver as a function of the time.
Figure 5:
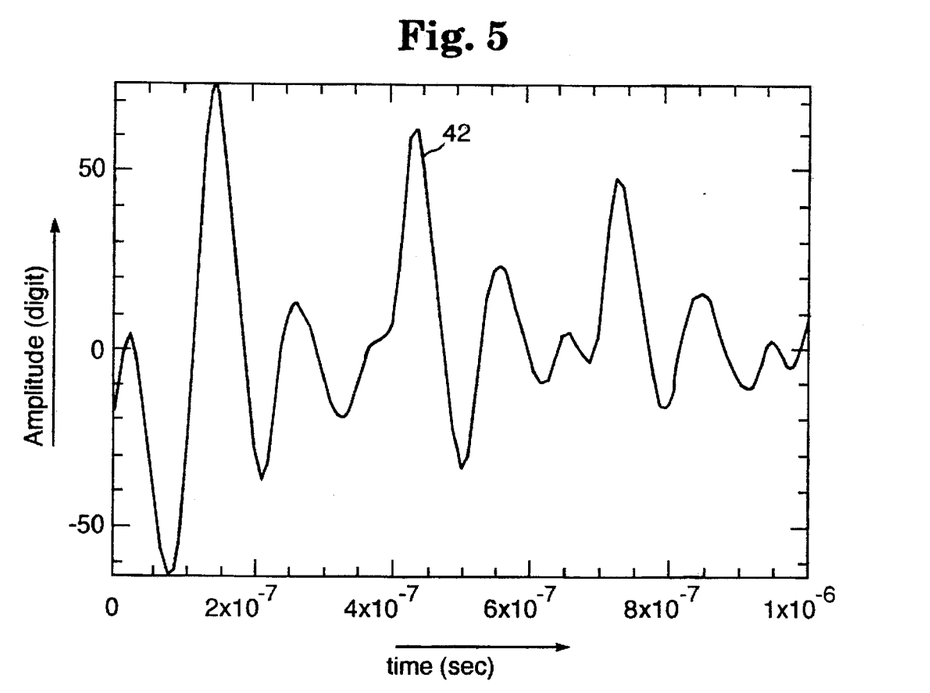
FIG. 5 shows a digitalized amplitude signal, received as a wall thickness echo sequence, as a function of the time.

FIG. 4 shows a typical echo signal (40) generated by a crack fault with its sample values, connected by straight lines in FIG. 4, as a function of the time t. FIG. 5 shows the sample values for a typical wall echo sequence (42) that are interconnected by straight lines, as a function of the time t. The equidistant sampling times shown in FIGS. 4 and 5 are achieved using commercially available sampling rates. It is clear that the sampling density in accordance with FIGS. 4 and 5 is not sufficient for precise determination of the maximum signal amplitude and of the time of occurrence of the maximum signal amplitude.

In order to achieve, using the commercially available modules for generation of the sampling rate and digitalization, a higher resolution with regard both to the maximum signal amplitude and to the timing of the signal amplitude, the function stored and given by the digital sample values is interpolated.

Interpolation is based on the knowledge that the electrical measurement signal with the time function f(t) at the connections of an ultrasonic testing head, e.g. of ultrasonic testing head (12), has the following properties:

$$|f(t)| < \epsilon_t, \text{ for } t < T_s \text{ und } t > T_e \qquad (1)$$

with $\epsilon_t$ as a barrier as small as required and $T_s$ and $T_e$ as the start and end times of the ultrasonic signal sequence.

Transformed into the frequency range, the following applies:

$$|F(\omega)| < \epsilon_\omega, \text{ for } \omega < \omega_s \text{ und } \omega > \omega_e \qquad (2)$$

with $\epsilon_\omega$ as a barrier as small as required and $\omega_s$ and $\omega_w$ as the lower and upper limit frequency.

Here, $F(\omega)$ is the Fourier transformation based on the following equation:

$$F(\omega) = \int_{-\infty}^{\infty} F(t) e^{i\omega t} \cdot dt \tag{3}$$

These are time-limited and band-limited signals.

The ultrasonic testing heads are generally vibration-capable, resonant structures of which the output voltages can be approximately described as amplitude-modulated sinusoidal vibrations and hence have the properties stated in the equations (1–3).

The time function f(t) is, in the case of the device shown in FIG. 1, present in the form of time-equidistant, discrete sample values, i.e. the following applies:

$$f(i\Delta t), \text{ for } i = 0, 1, \ldots M \tag{4}$$

The sampling intervals are sufficiently small, so that the following applies:

$$\frac{2\pi}{\Delta t} \ll \omega_e \tag{5}$$

When the condition set forth in (5) is met, the function values between the sampling times $n\Delta t$ and $(n+1)\Delta t$ can be ascertained by interpolation. After determining the parameters of the interpolation, the extreme values of the amplitudes and the delays until occurrence of the extreme values are stated analytically. A grade n polynomial is selected as the interpolation function.

Other functional approaches are possible, however these generally lead to a non-linear system of function equations that can only be solved iteratively—and hence in a calculation-intensive form. Using the polynomial:

$$P_N(t_i) = \sum_{n=0}^{N} a_n t_i^n, \; t_i = i\Delta t \tag{6}$$

the sum of the mean fault square is obtained.

$$F_Q = \sum_{i=0}^{M} (f(t_i) - P_N(t_i))^2 = \tag{7}$$

$$\sum_{i=0}^{M} \left\{ f^2(t_i) - 2 \sum_{n=0}^{N} a_n t_i^n f(t_i) + \sum_{n=0}^{N} a_n t_i^n \sum_{k=0}^{N} a_k t_i^k \right\}$$

From the requirement that the sum of the divergence squares be a minimum, the following results:

$$\frac{\partial F_Q}{\partial a_n} = \sum_{i=0}^{M} \left\{ -2 t_i^n f(t_i) + 2 \sum_{k=0}^{N} a_k t_i^{k+n} \right\} = 0; \tag{8}$$

$$n = 0, 1, 2 \ldots N$$

With the abbreviations $$b_{kn} = \sum_{i=0}^{M} t_i^{k+n} \text{ and } c_n = \sum_{i=0}^{M} f(t_i) t_i^n \tag{9}$$

the solution of the equation system in (8) can be provided:

$$a_k = b_{kn}^{-1} c_n; n = 0, 1, 2, \ldots N \tag{10}$$

with $b^{-1}{kn}$ to be understood as the elements of the inverse matrix associated with the matrix elements $b_{kn}$.

If N=M is selected, a strict interpolation results, i.e. $F_Q$=0. From M>N, a compensating curve is obtained and the interpolation is redundant with M<N.

The amplitude maximum is determined as follows:
First the time of the amplitude extreme is calculated from the following equation:

$$\frac{\partial P_N}{\partial t} = \sum_{n=0}^{N} n a_n t^{n-1} = 0 \tag{11}$$

For N=2, the following results with the coefficients $a_1$ and $a_2$:

$$t_0 = \frac{-a_1}{2a_2} \tag{12}$$

For N=3, it follows with the coefficients $a_1$, $a_2$ and $a_3$:

$$t_{1,2} = \frac{-a_2 \pm \sqrt{4a_2^2 - 3a_1 a_3}}{3a_3} \tag{13}$$

For N=4, three solutions are obtained with the Cardan solution formula. If N>4 is selected, the solution can generally only be determined iteratively (for example Björk—Anderson method).

The amplitude maximum is determined by incorporating the appropriate time value into the polynomial formulation given above in (6). A threshold value determination takes place in analogous form.

An additional difficulty in the determination of amplitudes and delays is encountered when the measured function values $f_M(t_i)$ are subject to a statistical uncertainty:

$$f_M(t_i) = f(t_i) + r(t_i) \tag{14}$$

In $r(t_i)$, all the error sources are summarized:
— discretization noise (AD converter)
— "ultrasonic grass" (structure noise)
— electronic noise (signal processing electronics)
— interference signals (crosstalk of surrounding electronics)

To reduce these error effects, the function $f_M(t_i)$ is subjected to filtering. In the frequency range, the following is obtained:

$$F_{fi}(\omega) = F_M(\omega) \tag{15}$$

and in the time range, with determination of the output signals using the convolution integral:

$$f_{fil}(t) = f_m(t) * h(t), \; bzw. \; f_{fil}(t) = \int_{-\infty}^{+\infty} f_m(\tau) h(t - \tau) d\tau \tag{16}$$

If filtering is only necessary within a short time, the convolution integral can be reduced approximately to a very limited integration and calculation interval. This is numerically simpler and faster than the calculation of the equations (15–16).

For the filter function, an ideal low-pass filter with the following transmission function is conceivable in the simplest case:

$$H(\omega) = \begin{cases} 1 & \text{for } |\omega| \leq \omega_{TP} \\ 0 & \text{otherwise} \end{cases} \tag{17}$$

A considerably better possibility is represented by a matched filter (or correlation filter):

$$h(t-\tau) = f_{sample}(\tau - t - t_0) \tag{18}$$

As $f_{sample}$, the first A-sample of a measurement series is used, for example. The time of the signal maximum is designated as $t_o$, so that the convolution result does not appear with a time lag.

Figure 6:
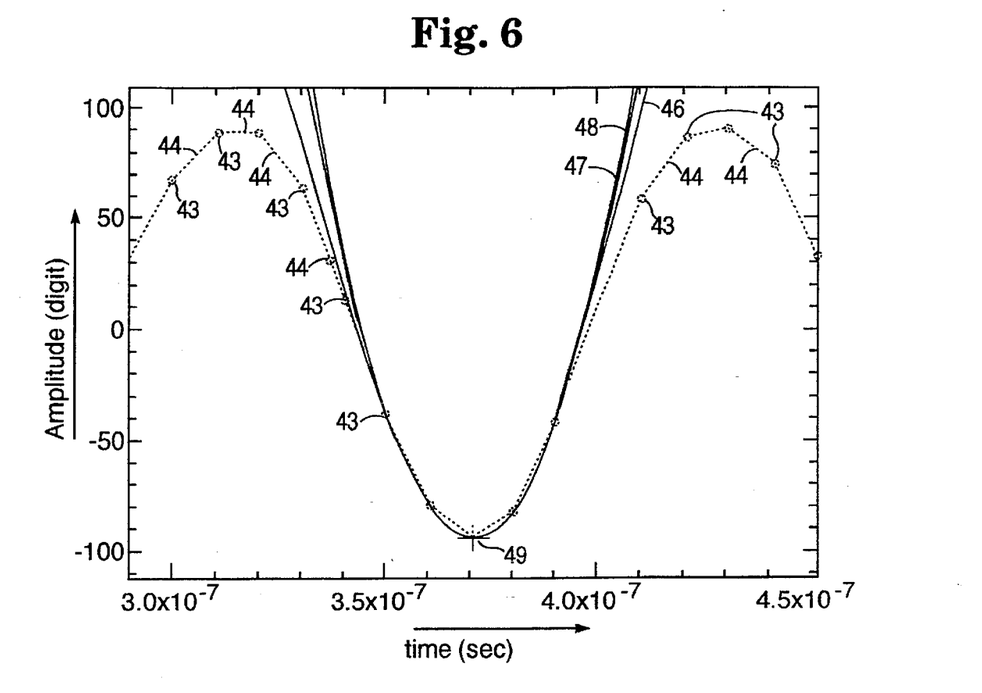
FIG. 6 shows a digitalized amplitude signal received as a crack fault echo, and an interpolation curve for the amplitude signal as a function of the time.

In FIG. 6, digitalized measurement values for a typical crack fault echo are marked in a diagram as crosses (43) and connected to one another by straight lines (44). This shows the course of the crack fault echo signal as a function of the time t, shown in the abscissa direction. Furthermore, interpolation curves (46), (47) and (48) are shown as a function of the time t in FIG. 6. The interpolation curves (46) to (48) were determined according to the polynomial formulation described above.

Furthermore, FIG. 6 shows the amplitude extreme (49) of the interpolation curves (46) to (48). A high resolution can be achieved using the amplitude extreme determined from the interpolation curves, as FIG. 6 shows.

Figure 7:
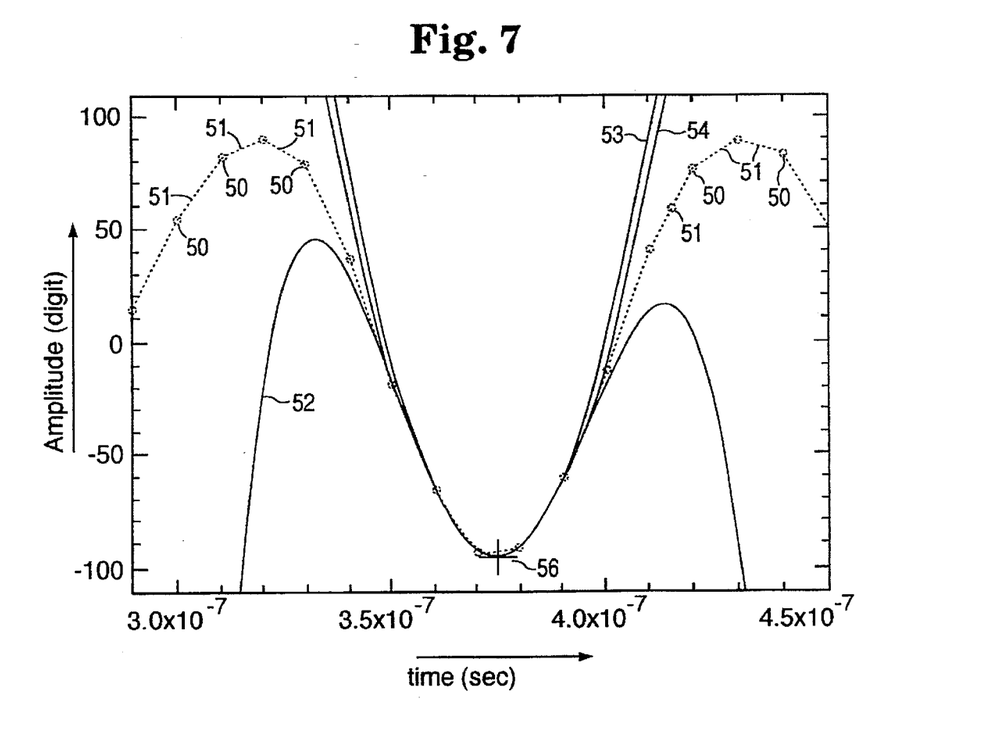
FIG. 7 shows a digitalized amplitude signal received as a wall thickness echo sequence, and an interpolation curve for the amplitude signal as a function of the time.

FIG. 7 shows digitalized measurement values for a typical wall thickness echo sequence, marked by crosses (50) in the diagram and joined up by straight lines (51).

This shows the course of the wall thickness echo sequence as a function of the time t, shown in the abscissa direction.

FIG. 7 also shows interpolation curves (52), (53), (54) as a function of the time t. The interpolation curves (52) to (54) were determined on the basis of the above interpolation formulation using the digitalized measurement values plotted in FIG. 7. The amplitude extreme (56) obtained on the basis of the interpolation curves (52) to (54) is also plotted in FIG. 7. This FIG. shows that with the interpolation curves the amplitude extreme can be determined with higher resolution than with the digital sample values alone.

Figure 8:
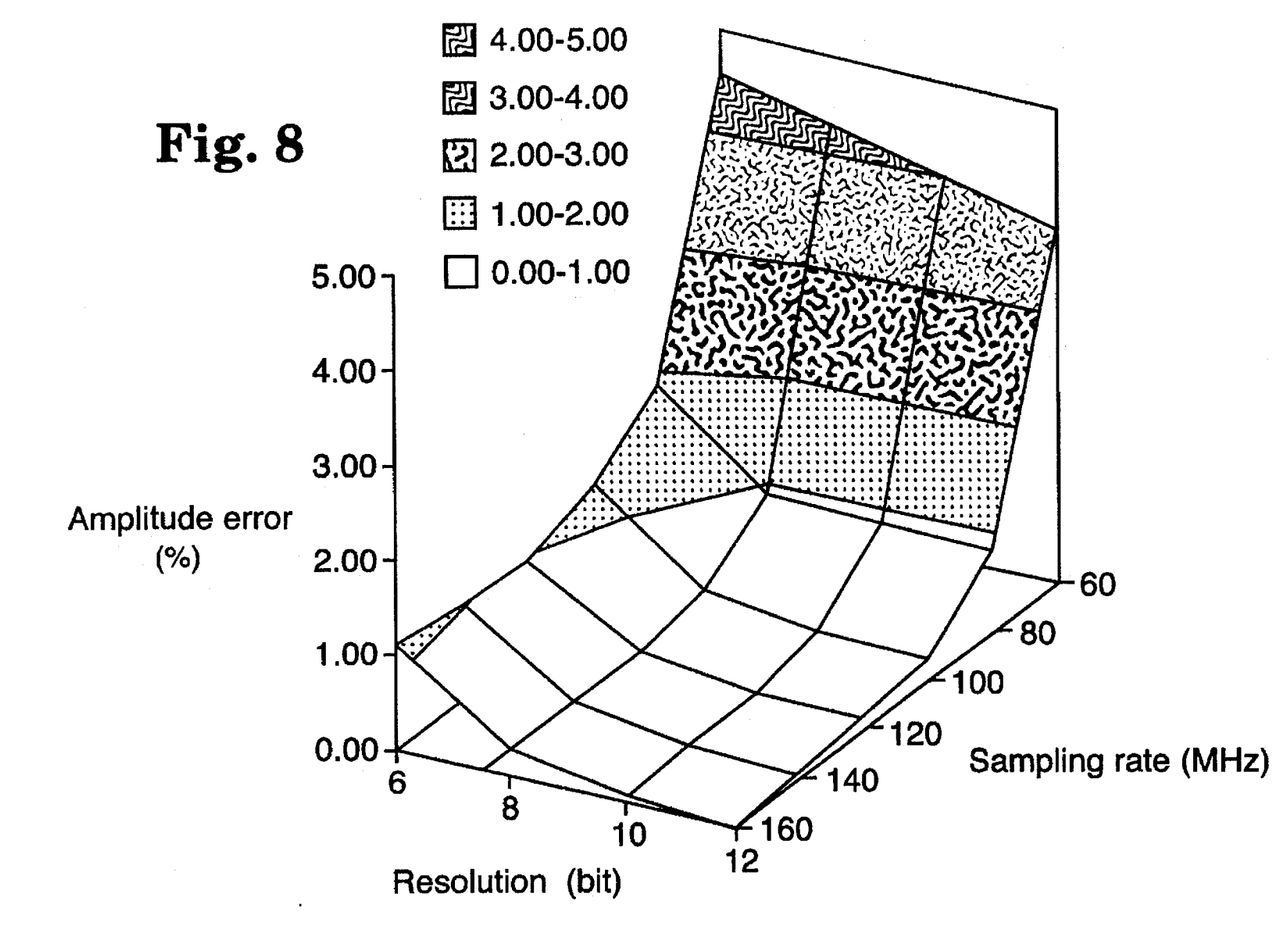
FIG. 8 shows the amplitude resolution of a certain interpolation method as a function of the sampling rate and of the resolution of the analog/digital converter.

The theoretically possible resolution by means of interpolation for the signal amplitude is shown in FIG. 8 in the three-dimensional diagram in % as a function of the sampling rate (sampling frequency) in MHz and of the resolution of the analog/digital converter (24) in bits.

Figure 9:
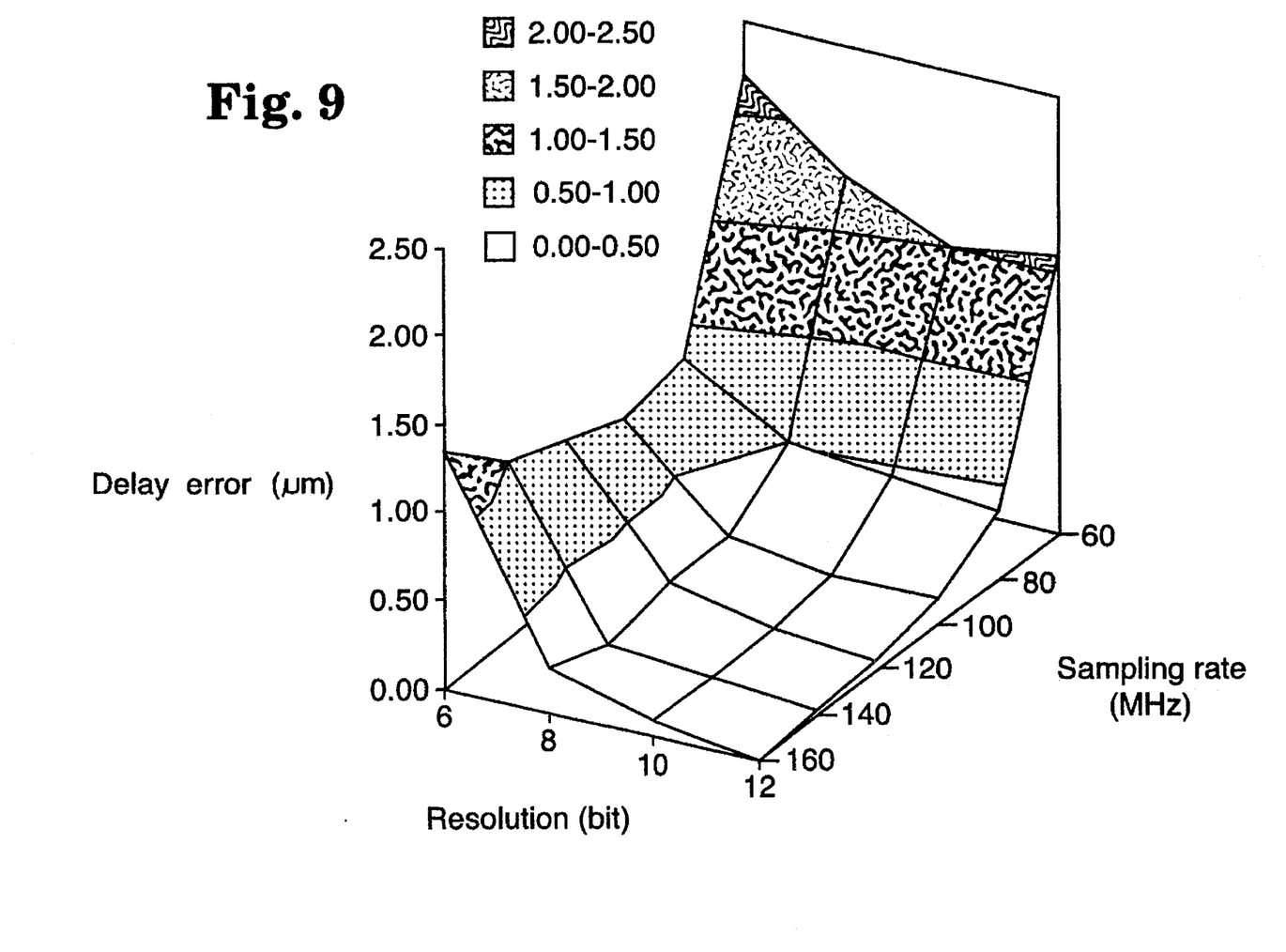
FIG. 9 shows the delay resolution of a certain interpolation method as a function of the sampling rate and of the resolution of the analog/digital converter.

FIG. 9 shows the resolution theoretically possible with interpolation for the delay of the ultrasonic signals in steel in μm as a function of the sampling rate (sampling frequency) in MHz and of the resolution of the analog/digital converter (24) in bits.

Several devices shown in FIG. 1 are best combined in one design unit, using which objects are non-destructively tested in several tracks. This allows an increase in the testing speed.

What is claimed is:

1. A method for use in non-destructive testing of objects using ultrasonics, comprising the steps of:

introducing ultrasonic pulses by an ultrasonic testing head into an object;

receiving by an ultrasonic testing head ultrasonic waves emitted by the object in response to the ultrasonic pulses and converting the ultrasonic waves into electrical signals having a signal sequence;

obtaining measurement values from said signals of said signal responses by time-equidistant sampling;

digitizing and storing said measurement values;

replacing a function represented by the digitized and stored measurement values by a Grade N polynomial according to the following equation:

$$P_N(t_i) = \sum_{n=0}^{N} a_n \cdot t_i^n, t_i = i\Delta t$$

wherein $t_i$ is the sampling time, for i=0, 1 . . . N, and $a_n$ the coefficients of the polynomial; and using said polynomial, determining with high resolution an amplitude extreme of the received ultrasonic waves and/or a delay of said ultrasonic wave with an amplitude extreme.

2. A method according to claim 1, wherein said delay of said ultrasonic wave is determined with the amplitude extreme from the first derivation of said Grade N polynomial based on time using the following equation:

$$\frac{\partial P_N}{\partial t} = \sum_{n=0}^{N} n a_n t^{(n-1)} = 0$$

and said amplitude extreme is determined by incorporation of the delay value into the equation $$P_N(t_i) = \sum_{n=0}^{N} a_n \cdot t_i^n$$

of said polynomial.

3. A method according to claim 1 or claim 2 wherein the electrical signals are sampled with a sampling rate between 60 and 120 MHz and are digitized with a resolution of eight to twelve bits.

4. A method according to claim 3, further comprising:

filtering said measurement values.

5. A method according to claim 4, wherein said filtering has a low-pass characteristic.

6. A method according to claim 4, wherein said filtering has a matched-filter characteristic.

7. A device for use in non-destructive testing of objects using ultrasonics, comprising:

an ultrasonic testing head for introducing ultrasonic pulses into an object and for receiving ultrasonic waves emitted by the object in response to the ultrasonic pulses and converting the ultrasonic waves into electrical signals having a signal sequence;

an amplifier for receiving said electrical signals;

an analog/digital converter;

a sample and hold circuit connected between the amplifier and the analog/digital converter and operating with a sampling rate in the range of 60 to 120 $MH_z$ to generate from said electrical signals measurements which are digitized by said analog/digital converter;

a write/read memory joined to said converter for storing said digitized measurement values; and a digital processor joined to the write/read memory for processing the stored digitized measurement values to replace said values by a Grade N polynomial according to the following equation:

$$P_N(t_i) = \sum_{n=0}^{N} a_n \cdot t_i^n, t_i = i\Delta t$$

wherein $t_i$ is the sampling time, for i=0, 1 . . . N, and $a_n$ the coefficients of the polynomial; and for using said polynomial to determine an amplitude extreme of the received ultrasonic waves and/or a delay of said ultrasonic wave with an amplitude extreme.

* * * * *